(12) United States Patent
Huber et al.

(10) Patent No.: US 10,522,876 B2
(45) Date of Patent: Dec. 31, 2019

(54) METHOD AND DEVICE FOR THE DETECTION OF CORROSION WITHIN AN AT LEAST PARTIALLY ELECTRICALLY CONDUCTIVE HOUSING OF AN ELECTRIC ENERGY STORAGE UNIT AND CORRESPONDING ELECTRIC ENERGY STORAGE SYSTEM

(71) Applicants: Robert Bosch GmbH, Stuttgart (DE); Lithium Energy and Power GmbH & Co. KG, Stuttgart (DE)

(72) Inventors: Bernhard Huber, Stuttgart (DE); Frank Stimm, Leonberg (DE); Peter Kohn, Stuttgart (DE); Ulrich Lange, Aichtal (DE)

(73) Assignees: Robert Bosch GmbH, Stuttgart (DE); Lithium Energy and Power GmbH & Co. KG, Stuttgart (DE)

( * ) Notice: Subject to any disclaimer, the term of this patent is extended or adjusted under 35 U.S.C. 154(b) by 178 days.

(21) Appl. No.: 15/662,507

(22) Filed: Jul. 28, 2017

(65) Prior Publication Data

US 2018/0040921 A1 Feb. 8, 2018

(30) Foreign Application Priority Data

Aug. 4, 2016 (EP) ..................................... 16182675

(51) Int. Cl.
*H01M 10/42* (2006.01)
*G01R 31/392* (2019.01)
(Continued)

(52) U.S. Cl.
CPC ........ *H01M 10/4228* (2013.01); *G01N 17/02* (2013.01); *G01R 31/392* (2019.01);
(Continued)

(58) Field of Classification Search
CPC .. H01M 10/4228; H01M 10/482; H01M 2/34; G01R 31/392; G01N 17/02
See application file for complete search history.

(56) References Cited

U.S. PATENT DOCUMENTS

| 5,036,287 A | 7/1991 | Serwatzky |
| 2015/0120225 A1* | 4/2015 | Kim ..................... G01R 31/392 702/63 |

FOREIGN PATENT DOCUMENTS

| CN | 103048376 A | * | 4/2013 |
| JP | 2012233702 A | * | 11/2012 |
| KR | 20160039663 | | 4/2016 |

* cited by examiner

*Primary Examiner* — Jonathan G Jelsma
(74) *Attorney, Agent, or Firm* — Michael Best & Friedrich LLP

(57) ABSTRACT

Detection of corrosion within an at least partially electrically conductive housing of an electric energy storage unit. The electric energy storage unit has a positive terminal and a resistance element between the positive terminal and the housing. State of charge values of the electric energy storage unit for at least one first instant of time and at least one second instant of time are determined. An electrical isolation resistance value between the housing of the electric energy storage unit and at least one reference point for at least one third instant of time may also be determined. A first comparison of a difference of the determined state of charge values with a predefined state of charge difference value for the electric energy storage unit and/or a second comparison of the determined electrical isolation resistance value with a predefined electrical isolation resistance value for the electric energy storage unit are performed.

12 Claims, 3 Drawing Sheets

(51) Int. Cl.
*G01N 17/02* (2006.01)
*H01M 2/34* (2006.01)
*H01M 10/48* (2006.01)
*H02J 7/00* (2006.01)

(52) U.S. Cl.
CPC ........... H01M 2/34 (2013.01); H01M 10/482 (2013.01); *H01M 2200/00* (2013.01); *H02J 7/0029* (2013.01)

METHOD AND DEVICE FOR THE DETECTION OF CORROSION WITHIN AN AT LEAST PARTIALLY ELECTRICALLY CONDUCTIVE HOUSING OF AN ELECTRIC ENERGY STORAGE UNIT AND CORRESPONDING ELECTRIC ENERGY STORAGE SYSTEM

BACKGROUND OF THE INVENTION

The present invention emanates from a method and a device for the detection of corrosion in an at least partially electrically conductive housing of an electric energy storage unit as well as an electric energy storage system.

In many applications, e.g. in the automobile field, battery cells, which are based on lithium-ion technology, have a metallic housing. This provides mechanical stability and prevents liquids from entering into electrically sensitive areas. This is especially important in the automotive field where safety requirements are high and must not be compromised as lives could be at stake. However, under certain conditions, the metallic housing is prone to electrochemical reactions which may occur inside the cell, for example in areas of the housing which are in contact with an electrolyte. Electric potential gradients within a battery cell may enable these reactions which can lead to corrosion from the inside of the battery cell. Finally, this may even cause leakage of the battery cell. It is therefore essential to detect a possible corrosion problem early in its development to be able to carry out necessary measures.

The document DE 3904894 C1 describes a method and a device for the determination of corrosion on components. To this end, an electrically conductive measuring wire is installed alongside the component which is monitored for corrosion. The electrically conductive measuring wire is hence also exposed to a possibly corrosive environment. By analyzing the electrical resistance of the measuring wire, corrosion can be detected and analyzed.

SUMMARY OF THE INVENTION

According to the present invention, a method and a device for the detection of corrosion in an at least partially electrically conductive housing of an electric energy storage unit as well as an electric energy storage system.

The method for the detection of corrosion in an at least partially electrically conductive housing of an electric energy storage unit comprises several steps and the electric energy storage unit has a positive terminal and features a resistance element with a preassigned electrical resistance value between the positive terminal and the at least partially electrically conductive housing. The method comprises determining state of charge values of the electric energy storage unit for at least one first instant of time and at least one second instant of time and/or determining an electrical isolation resistance value between the housing of the electric energy storage unit and at least one reference point which is situated outside of the electric energy storage unit for at least one third instant of time. The method further comprises a first comparison of a difference of the determined state of charge values with a predefined state of charge difference value for the electric energy storage unit and/or a second comparison of the determined electric isolation resistance value with a predefined electric isolation resistance value for the electric energy storage unit. Depending on the first comparison result and/or the second comparison result a signal is generated concerning the detection of corrosion.

The predefined values act as thresholds to assess the occurence of corrosion. This is advantageous because determining the state of charge values and determining the electrical isolation resistance value are already available functionalities which are used here in combination with carefully predefined values so that additional information can be extracted apart from the mere numerical values. The determination and comparison of the state of charge values is particularly well suited when a state of charge determination uncertainty, i.e. the uncertainty to which the real state of charge can be determined and distinguished from other state of charge values, is low, i.e. the state of charge value can be determined with high accuracy and reliably distinguished from other state of charge values because an inherent imprecision or uncertainty of the determined state of charge value is low. In conjunction with a low self-discharge current of the electric energy storage unit, this creates favorable conditions for this variant. Another variant, relying on the determination of the electrical isolation resistance value, will always detect corrosion but also other electrical isolation fault cases. Combining the advantages of both variants is another variant improving reliability and discrimination power of different fault cases.

As an alternative, all state of charge values may be transformed into open circuit voltage values and/or state of charge difference values may be transformed into open circuit voltage difference values.

Preferably, the electric energy storage unit is a lithium based battery cell, e.g. a lithium-ion battery cell, whose housing may preferably be partially or completely composed of aluminum. Other metals may be used as well. The purity of the used materials may be set by corresponding industry norms. This is advantageous because these types of electric energy storage units are widely used and therefore well suited for the application of the method according to the invention.

In a further embodiment in case of the first comparison, an electric current flown from or to the electric energy storage unit between the at least one first instant of time and the at least one second instant of time is accounted for in the first comparison. This allows a better distinction between predefined permissible and non-permissible state of charge difference values than a fixed predefined state of charge difference value. For example, when an electric current flows from or to the electric energy storage unit due to use between the first instant of time and the second instant of time, for example to power an electric engine, the amount of charge flown has to be taken into account in the first comparison. The amount of charge flown can be calculated by the integral of current over time. The value of the integral is then divided by a capacity value of the electric energy storage unit and then subtracted from the difference of the determined state of charge values to account for the amount of charge flown due to use of the electric energy storage unit. The remaining state of charge difference is then compared with the predefined state of charge difference value which is, for example, due to corrosion.

In a further embodiment in case of the first comparison, the predefined state of charge difference value for the electric energy storage unit is dependent on a time difference between the at least one first instant of time and the at least one second instant of time. This allows a better distinction between predefined permissible and non-permissible state of charge difference values than a fixed predefined state of charge difference value. Depending on the time difference, a particular predefined state of charge difference value is used in the corresponding comparison. The respective predefined state of charge difference values may be stored in a memory, for example in the form of a characteristic map. As the time difference is generally not exactly known beforehand, e.g. at design time of the electric energy storage unit, this dependence conveys the needed flexibility to cope with the dynamics and changing environment of an application in practice.

In a further embodiment of the method in case of the determination of the state of charge values, before the determination of the states of charge, it is verified that a current flowing from or to the electric energy storage unit is above a predefined lower threshold and below a predefined upper threshold. The absolute value of the predefined lower and predefined upper threshold may be identical. This improves the accuracy of the state of charge determination process and as a consequence the corrosion detection process. The time of no use required before the determination process begins may vary depending on the actual implementation but may be chosen in the range of several minutes, typically 1 to 10 minutes. It is to be noted that in an implementation of the proposed method in a vehicle there will almost always flow a small current to power electronic devices such as the vehicle's electronic control unit. To allow for these small currents, typically below one or two amps, e.g. 500 mA, the predefined thresholds may be chosen accordingly.

Additionally, in case of the determination of the state of charge values, the electric energy storage unit may be controlled before the determination of the state of charge values in such a way that the current flowing from or to the electric energy storage unit is above the predefined lower threshold and below the predefined upper threshold at the at least one first instant of time and the at least one second instant of time and in between these at least two instants of time. This improves the accuracy of the state of charge determination process and as a consequence the corrosion detection process.

In addition to that, the electric energy storage unit may be controlled in such a way that it has not been in use for some time period directly before the determination process. The advantages from the paragraph before apply likewise.

Additionally, the control of the electric energy storage unit may prevent a charge balancing operation between the electric energy storage unit and further electric energy storage units. A charge balancing operation is typically performed between electric energy storage units to equalize their state of charge. For this purpose, additional hardware may be installed in order to bypass or discharge selected energy storage units in a controlled way. This prevents obscuring a discharge of the electric energy storage unit caused by corrosion and hence guarantees favorable conditions for the method to perform as intended.

Additionally, in case of the determination of the state of charge values, the time difference between the at least one first instant of time and the at least one second instant of time is chosen in consideration of the preassigned electrical resistance value and the state of charge determination uncertainty respectively a state of charge determination uncertainty threshold. This allows a fine tuning of the proposed method by relating hardware properties, e.g. voltage measurement accuracy and/or current measurement accuracy, with method properties, e.g. the time difference. Furthermore, the state of charge determination uncertainty may vary depending on, for example, driving situations of a vehicle. The state of charge determination uncertainty may, for example, vary between 0% and 5%, with a typical value of 2%. This value is also called the state of charge determination uncertainty threshold. Therefore, a change in state of charge of more than 2% can reliably be detected. Hence, the method is flexible enough to adapt to changing conditions as opposed to a preset time difference.

Additionally, in case of the determination of the state of charge values and the determination of the electrical isolation resistance value, the at least one third instant of time may coincide with the at least one first instant of time or the at least one second instant of time. This speeds up the detection of corrosion.

Additionally, in case of the determination of the electrical isolation resistance value, a future evolution of the electrical isolation resistance value may be forecast using the determined at least one third electrical isolation resistance value. Using the forecast, a fourth instant of time for a further determination of the electrical isolation resistance value between the housing and the at least one reference may be scheduled. Thus, when a predefined critical level of the electrical isolation resistance value will be reached, the determination can be performed more often to more closely survey the electrical isolation resistance value. Before this point in time, a sporadic determination may be sufficient. Furthermore, this even allows to prearrange a repair shop appointment as a time period can be determined where safe operation of the electric energy store unit is not at risk or possibly dangerous. Thus, unnecessary checks of the electric energy storage unit can be avoided and additional service can be provided to the owner of the electric energy storage unit.

Additionally, in case of the determination of the electrical isolation resistance value, the at least one reference point, which is situated outside of the electric energy storage unit, is at a ground potential. This simplifies the determination of the electrical isolation resistance value as it is common, e.g. in vehicles, to have a defined ground potential. Furthermore, for the predetermination of the predefined electric isolation value, it is necessary to have a common reference basis.

Furthermore, a device for the detection of corrosion within an at least partially electrically conductive housing of an electric energy storage unit is provided, where the electric energy storage unit has a positive terminal and features a resistance element with a preassigned electrical resistance value between the positive terminal and the at least partially electrically conductive housing. The device comprises an electronic control unit and is configured to perform all of the steps of the method according to the invention. It is possible that the device is identical with the electronic control unit and that the steps of the method are performed on the electronic control unit. This may be the case in particular in the automotive field, where electric energy storage systems typically comprise an electronic battery management system unit. The advantages as mentioned above apply likewise.

Furthermore, an electric energy storage system comprising several electric energy storage units and a device according to the invention is provided, wherein at least one electric energy storage unit has an at least partially electrically conductive housing and a positive terminal and features a resistance element with a preassigned electrical resistance value between the positive terminal and the at least partially conductive housing. The advantages as mentioned above apply likewise.

DETAILED DESCRIPTION

Advantageous embodiments of the invention are given in the figures and described in detail in the description below.

FIG. 1 shows an electric energy storage unit, which has a positive terminal and a negative terminal and features a resistance element with a preassigned electrical resistance value between the positive terminal and its electrically conductive housing.

FIG. 2 visualizes different combinations of preassigned electrical resistance values for a resistance element, possible corrosion currents and resulting corrosion detection times.

FIG. 3 visualizes different combinations of the preassigned electrical resistance values, electrical isolation resistance values and an effect of an electrical isolation failure monitoring threshold.

DETAILED DESCRIPTION

Identical reference signs refer to identical features in all figures.

Figure 1:
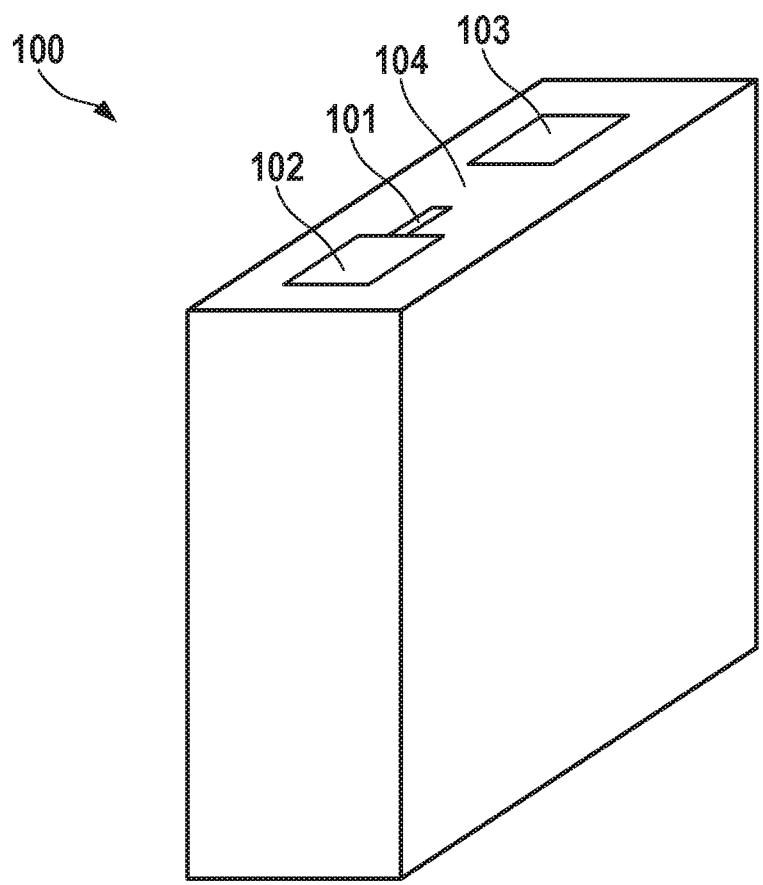

FIG. 1 shows an electric energy storage unit 100, which has a positive terminal 102 and a negative terminal 103. The electric energy storage unit 100, which in this embodiment is a battery cell, 100 further comprises a metallic housing 104. A resistance element 101 with a preassigned electrical resistance value is installed between the positive terminal 102 and the metallic housing 104 which electrically connects the metallic housing 104 and the positive terminal 102. In this embodiment, an explicit electrical component, for example a resistor with a preassigned electrical resistance value, is used. However, the resistance element 101 may also be embodied by a well-designed interface between the housing 104 and electrochemically active parts, like the jellyroll, of the battery cell. Well-designed in this context means that the resistance value between the interfaces is constant or only varies slightly. A variant, which is not shown here, only has a partially conductive housing 104, i.e. only parts of the housing are electrically conductive and other parts are not.

Figure 2:
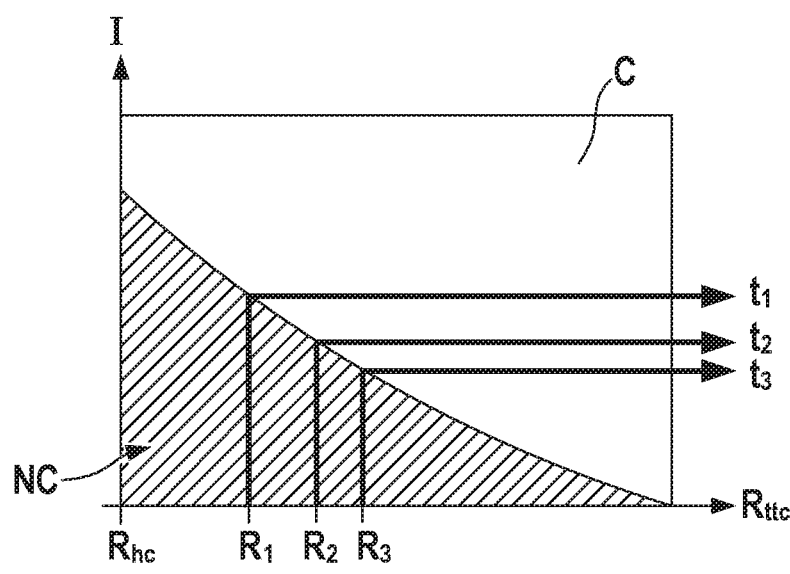

FIG. 2 shows different combinations of the preassigned electrical resistance values $R_{ttc}$ for the resistance element 101, currents I between the positive terminal 102 and the housing 104 of the electric energy storage unit 100 and resulting corrosion detection times. The X-axis represents a preassigned electrical resistance value $R_{ttc}$ for the resistance element 101 and the Y-axis on the left represents a current value I, which flows from the positive terminal 102 to the housing 104 of the electric energy storage unit 100. The shaded area NC gives combinations of preassigned electrical resistance values $R_{ttc}$ and current values I, for which no corrosion occurs. The white area C gives combinations of preassigned electrical resistance values $R_{ttc}$ and current values I for which corrosion is possible. These relations may be determined beforehand, i.e. before the actual use of the electric energy storage unit 100 in, for example, a vehicle, via simulations or experimental investigations. As a battery management system normally has a certain uncertainty with regard to state of charge determination, which is expressed by a certain state of charge determination uncertainty threshold, the preassigned electrical resistance value $R_{ttc}$ cannot be chosen arbitrarily high as this would lead to very small currents I flowing between the positive terminal 102 and the housing 104. This, in return, would only lead to a negligible state of charge difference within reasonable time. Furthermore, a self-discharge current, which is inherent to most, if not all electric energy storage units, may obscure a possible discharge by corrosion. These effects and the state of charge determination uncertainty threshold have to be taken into account when selecting an appropriate preassigned electrical resistance value $R_{ttc}$. Three different cases are highlighted in FIG. 2, where a certain state of charge determination uncertainty threshold is assumed. When selecting a first preassigned electrical resistance value $R_1$, the time that has to pass between the first instant of time and the second instant of time, when state of charge measurements are taken, is a first time period $t_1$. The first time period $t_1$ is shown on the right with an arrow indicating the relationship between the electrical resistance value $R_1$ and the corresponding first time period $t_1$ needed for the detection of corrosion. When selecting a second preassigned electrical resistance value $R_2$, the time that has to pass between the first instant of time and the second instant of time, when state of charge measurements are taken, is a second time period $t_2$. When selecting a third preassigned electrical resistance value $R_3$, the time that has to pass between the first instant of time and the second instant of time, when state of charge measurements are taken, is a third time period $t_3$. The first time period $t_1$ is shorter than the second time period $t_2$ which again is shorter than the third time period $t_3$ due to the different currents flowing. Depending on the actual capabilities of the battery management system concerning state of charge uncertainty and in particular the state of charge determination uncertainty threshold, i.e. its capability to reliably distinguish between different SOC values, an appropriate preassigned electrical resistance value may be chosen for the resistance element 101. The relationship between the preassigned electrical resistance values $R_{ttc}$, the currents I between the positive terminal 102 and the housing 104 of the electric energy storage unit 100 and the resulting corrosion detection times, i.e. the corresponding time periods or time differences needed for the detection of corrosion, may be determined via measurements or simulations or a combination thereof and may be stored in a memory, for example of a battery management system. Therefore, a corresponding time period or time difference need for the detection of corrosion is assigned to each preassigned electrical resistance value $R_{ttc}$. These time periods or time differences also depend, as mentioned above, on the state of charge determination uncertainty threshold. $R_{hc}$ represents a resistance value when there is a so-called hard connection of the housing 104 and the positive terminal 102, i.e. there is virtually no electrical resistance. One should keep in mind when choosing an appropriate resistance value that small values of $R_{ttc}$, like the value $R_{hc}$, may result in high short-circuit currents in case of certain failure cases, which may pose a certain risk of compromising safety.

Figure 3:
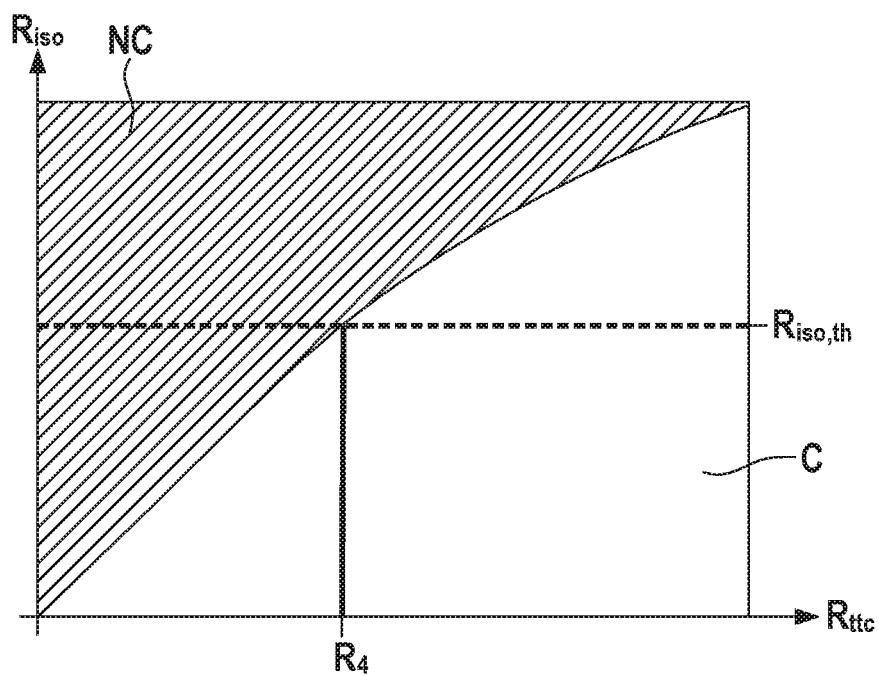

FIG. 3 shows different combinations of the preassigned electrical resistance values $R_{ttc}$ for the resistance element 101, electrical isolation resistance values $R_{iso}$ and an effect of an electrical isolation failure monitoring threshold $R_{iso,th}$. The X-axis represents a preassigned electrical resistance value $R_{ttc}$ and the Y-axis represents an electrical isolation resistance value $R_{iso}$ between the housing 104 of the electric energy storage unit 100 and a certain reference potential, e.g. ground potential. The shaded area NC gives combinations of preassigned electrical resistance values $R_{ttc}$ and electrical isolation resistance values $R_{iso}$, for which no corrosion occurs and the white area C gives combinations of preassigned electrical resistance values $R_{ttc}$ and electrical isolation resistance values $R_{iso}$ for which corrosion occurs. A threshold for the detection of an electrical isolation failure is assumed to be given by $R_{iso,th}$. Below this threshold, an electrical isolation failure is detected. This leads to an upper limit $R_4$ on the preassigned electrical resistance value $R_{ttc}$. Hence, if the electrical isolation resistance value $R_{iso}$ drops below the threshold $R_{iso,th}$ and the preassigned electrical resistance value $R_{ttc}$ has been chosen to the corresponding limit value $R_4$, corrosion can be detected accordingly. To be able to perform the electrical isolation monitoring, a battery management system or any other device in a system, where the method according to the invention shall be performed, needs the corresponding capability. Another underlying assumption for FIG. 3 is that housing isolation failures leading to corrosion are always via the ground potential. If the preassigned electrical resistance value $R_{ttc}$ is chosen equal or smaller than the upper limit value $R_4$, no undetected corrosion is supposed to happen. However, a detected electrical isolation fault does not necessarily imply corrosion. The relationship between the preassigned electrical resistance values $R_{ttc}$, the preassigned electrical resistance values $R_{iso}$ and the effect of the electrical isolation resistance monitoring threshold $R_{iso,th}$ may be determined via measurements or simulations or a combination thereof and may be stored in a memory, for example of a battery management system.

Figure 4:
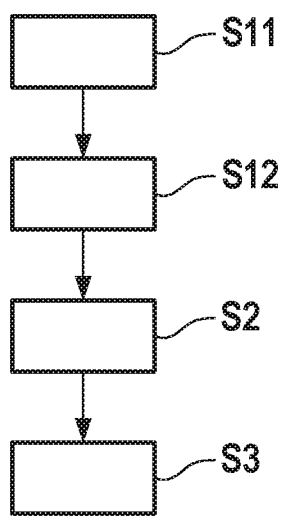
FIG. 4 shows a flow diagram of a first embodiment of the method according to the invention.

FIG. 4 shows a flow diagram of a first embodiment of the method according to the invention. In a first step S11, state of charge values of an electric energy storage unit are determined for at least one first instant of time and at least one second instant of time. In a second step S12, an electrical isolation resistance value between a housing of the electric energy storage unit and at least one reference point which is situated outside of the electric energy storage unit is determined for at least one third instant of time. The first step S11 and the second step S12 may also be performed in reversed order. Furthermore, the third instant of time may be identical with the first instant of time and/or the second instant of time. In a third step S2, a first comparison of a difference of the determined state of charge values with a predefined state of charge difference value for the electric energy storage unit and a second comparison of the determined electrical isolation resistance value with a predefined electrical isolation resistance value for the electric energy storage unit is performed. The information needed is comparable to the one given in FIGS. 2 and 3. In a fourth step, a signal concerning the detection of corrosion is generated depending on the first comparison result and the second comparison result.

Figure 5:
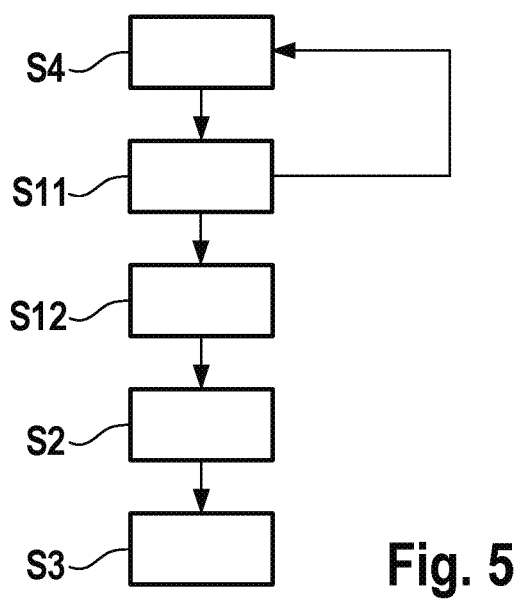
FIG. 5 shows a flow diagram of a second embodiment of the method according to the invention.

FIG. 5 shows a flow diagram of a second embodiment of the method according to the invention. In a fifth step S4, which is performed before the first step S11, it is verified that the electric energy storage unit is not used electrically. This may comprise a certain usage threshold. For example, it may be allowed that a small current is drawn or supplied from/to the electric energy storage unit. This current is preferably in the absolute range of 0 to 5 amps, possibly 0 to 2 amps or 0 to 0.5 amps, which then represent, with correct sign, the predefined lower threshold and the predefined upper threshold. This is due to the fact that for example a battery management system has to be supplied with electric energy. After this, in the first step S11, a determination of a state of charge value is performed for a first instant of time. Then, it is again verified in the fifth step S4, that the electric energy storage unit is not used electrically whereupon the first step S11 is performed for a second instant of time. Preferably, the electric energy storage unit is not used electrically on and between the first and second instant of time. The ensuing steps have been described above.

Figure 6:
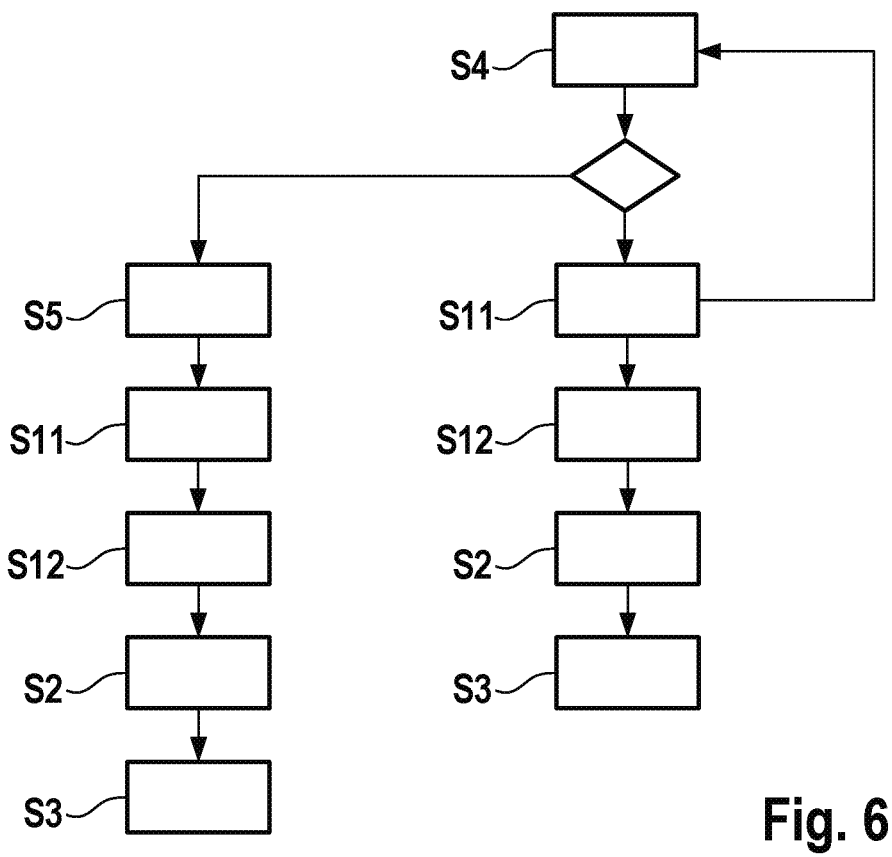
FIG. 6 shows a flow diagram of the third embodiment of the method according to the invention.

FIG. 6 shows a flow diagram of a third embodiment of the method according to the invention. In the fifth step S4, it is verified that the electric energy storage unit is not used electrically. If the verification succeeds, the steps which have already been described in the context of FIG. 5 are performed. If the verification fails, a sixth step S5 is performed, where the electric energy storage unit is controlled in such a way before the determination of the state of charge values that the electric energy storage unit is not used electrically in a substantial way at the at least one first instant of time and the at least one second instant of time and in between these at least two instants of time. "In a substantial way" may therefore refer to the current ranges given before. The control may comprise opening switches in an electric energy storage system which comprises the electric energy storage unit. As an alternative, this may also be realized in software by deactivating certain functions, for example additional energy sources like entertainment systems and heating. When the sixth step S5 has been completed, the steps that have been introduced above ensue.

The invention claimed is:

1. A method for the detection of corrosion within an at least partially electrically conductive housing (104) of an electric energy storage unit (100), the electric energy storage unit (100) having a positive terminal (102) and a resistance element (101) with a preassigned electrical resistance value ($R_{ttc}$, $R_1$, $R_2$, $R_3$, $R_4$) between the positive terminal (102) and the at least partially electrically conductive housing (104), the method comprising:
   determining state of charge values of the electric energy storage unit (100) for at least one first instant of time and at least one second instant of time;
   determining an electrical isolation resistance value ($R_{iso}$) between the housing (104) of the electric energy storage unit (100) and at least one reference point which is situated outside of the electric energy storage unit (100) for at least one third instant of time;
   performing a first comparison of a difference of the determined state of charge values with a predefined state of charge difference value for the electric energy storage unit (100);
   performing a second comparison of the determined electrical isolation resistance value ($R_{iso}$) with a predefined electrical isolation resistance value ($R_{iso,th}$) for the electric energy storage unit (100); and
   generating a signal concerning the detection of corrosion depending on the first comparison and the second comparison.

2. The method according to claim 1, where an electric current flown from or to the electric energy storage unit between the at least one first instant of time and the at least one second instant of time is accounted for in the first comparison.

3. The method according to claim 1, where the predefined state of charge difference value for the electric energy storage unit (100) is dependent on a time difference ($t_1$, $t_2$, $t_3$) between the at least one first instant of time and the at least one second instant of time in the first comparison.

4. The method according to claim 1, further comprising:
   verifying before the determining the state of charge values that an electric current flowing from or to the electric energy storage unit (100) is above a predefined lower threshold and below a predefined upper threshold.

5. The method according to claim 1, further comprising:
   controlling the electric energy storage unit (100) before the determination of the state of charge values in such a way that the electric current flowing from or to the electric energy storage unit (100) is above the predefined lower threshold and below the predefined upper threshold at the at least one first instant of time and the at least one second instant of time and in between these at least two instants of time.

6. The method according to claim 5, further comprising controlling the electric energy storage unit (100) to prevent a charge balancing operation between the electric energy storage unit (100) and further electric energy storage units (100).

7. The method according to claim 1, wherein determining state of charge values includes choosing a time difference ($t_1, t_2, t_3$) between the at least one first instant of time and the at least one second instant of time based on the preassigned electrical resistance value ($R_{ttc}, R_1, R_2, R_3, R_4$) and a state of charge determination uncertainty.

8. The method according to claim 1, wherein the at least one third instant of time coincides with the at least one first instant of time or with the at least one second instant of time.

9. The method according to claim 1, further comprising:
forecasting a future evolution of the electrical isolation resistance value ($R_{iso}$) using the determined electrical isolation resistance value ($R_{iso}$);
using the forecast to schedule a fourth instant of time for a further determination of the electrical isolation resistance value ($R_{iso}$) between the housing (104) and the at least one reference point which is situated outside of the electric energy storage unit (100).

10. The method according to claim 1, wherein the at least one reference point, which is situated outside of the electric energy storage unit (100), is at a ground potential.

11. A device for the detection of corrosion within an at least partially electrically conductive housing (104) of an electric energy storage unit (100), the electric energy storage unit (100) having a positive terminal (102) and featuring a resistance element (101) with a preassigned electrical resistance value ($R_{ttc}, R_1, R_2, R_3, R_4$) between the positive terminal (102) and the at least partially electrically conductive housing (104), where the device comprises an electronic control unit and is configured to
determine state of charge values of the electric energy storage unit (100) for at least one first instant of time and at least one second instant of time,
determine an electrical isolation resistance value ($R_{iso}$) between the housing (104) of the electric energy storage unit (100) and at least one reference point which is situated outside of the electric energy storage unit (100) for at least one third instant of time,
perform a first comparison of a difference of the determined state of charge values with a predefined state of charge difference value for the electric energy storage unit (100),
perform a second comparison of the determined electrical isolation resistance value ($R_{iso}$) with a predefined electrical isolation resistance value ($R_{iso}$,th) for the electric energy storage unit (100), and
generate a signal concerning the detection of corrosion depending on the first comparison result and the second comparison result.

12. An electric energy storage system, comprising several electric energy storage units (100) and a device according to claim 11, wherein at least one electric energy storage unit (100) has an at least partially electrically conductive housing (104) and a positive terminal (102) and features a resistance element (101) with a preassigned electrical resistance value ($R_{ttc}, R_1, R_2, R_3, R_4$) between the positive terminal (102) and the at least partially electrically conductive housing (104).

\* \* \* \* \*